United States Patent [19]

Tomita

[11] 4,114,039
[45] Sep. 12, 1978

[54] X-RAY APPARATUS

[75] Inventor: Chuji Tomita, Tokyo, Japan

[73] Assignee: Hitachi Medical Corporation, Tokyo, Japan

[21] Appl. No.: 740,720

[22] Filed: Nov. 10, 1976

[51] Int. Cl.² .................. G01N 21/00; G01N 21/34
[52] U.S. Cl. ........................ 250/439 R; 250/445 R
[58] Field of Search .................. 250/439, 444, 445

[56] References Cited

U.S. PATENT DOCUMENTS

| 2,534,623 | 12/1950 | Pitts et al. | 250/439 |
| 3,532,882 | 10/1970 | Craig et al. | 250/439 |

FOREIGN PATENT DOCUMENTS 26,761  1/1964  German Democratic Rep. ..... 250/444

Primary Examiner—Alfred E. Smith
Assistant Examiner—T. N. Grigsby

[57] ABSTRACT

An X-ray apparatus constituted by a roentgenographic pedestal having a patient's table on top thereof; a supporting member secured on the pedestal and extending in the direction away from the surface of the table and having an end surface arranged so that this end surface is allowed to change its position progressively as desired while being in contact with rollers provided on a base frame of the apparatus and that the direction of movement of the pedestal is restricted by the supporting member. The roentgenographic pedestal, therefore, is movable along the contour of the surface of contact of the end surface of the supporting member, and furthermore this pedestal itself is capable of assuming either a horizontal position, an inclined position or a vertical position, as desired. In the horizontal position of the pedestal, the distance between the surface of the table and the floor on which the apparatus is installed can be greatly reduced.

5 Claims, 9 Drawing Figures

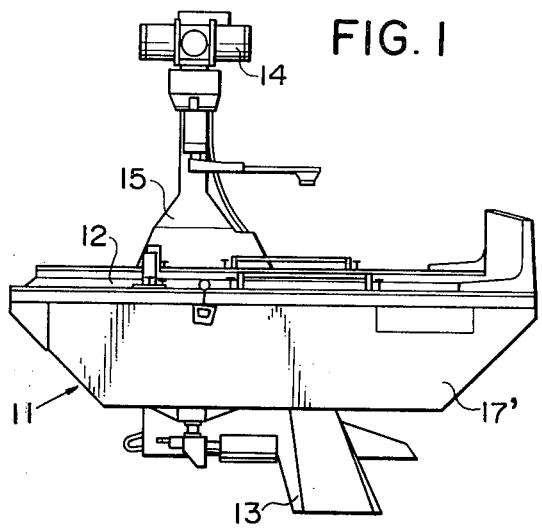
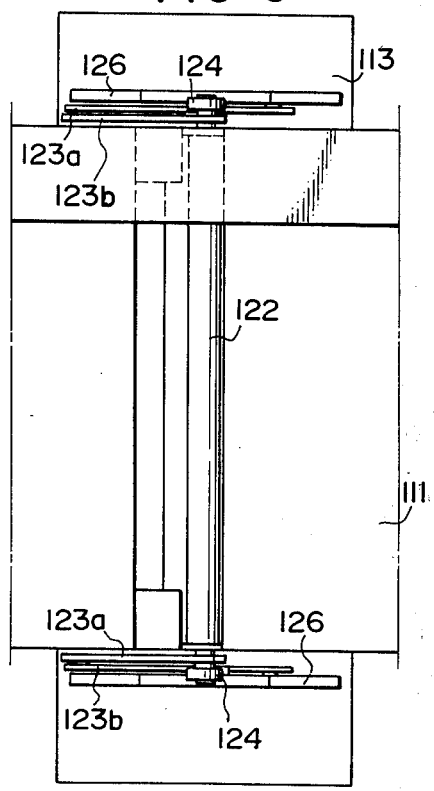
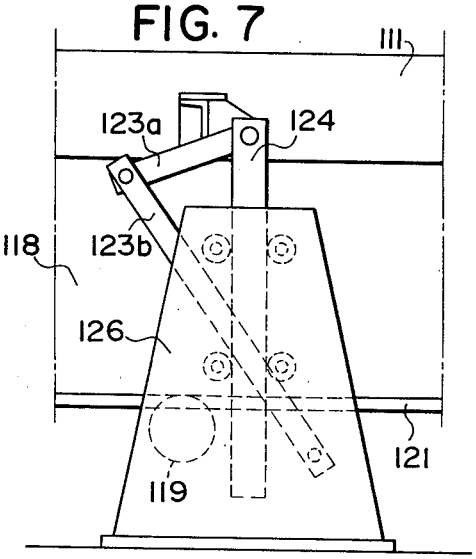

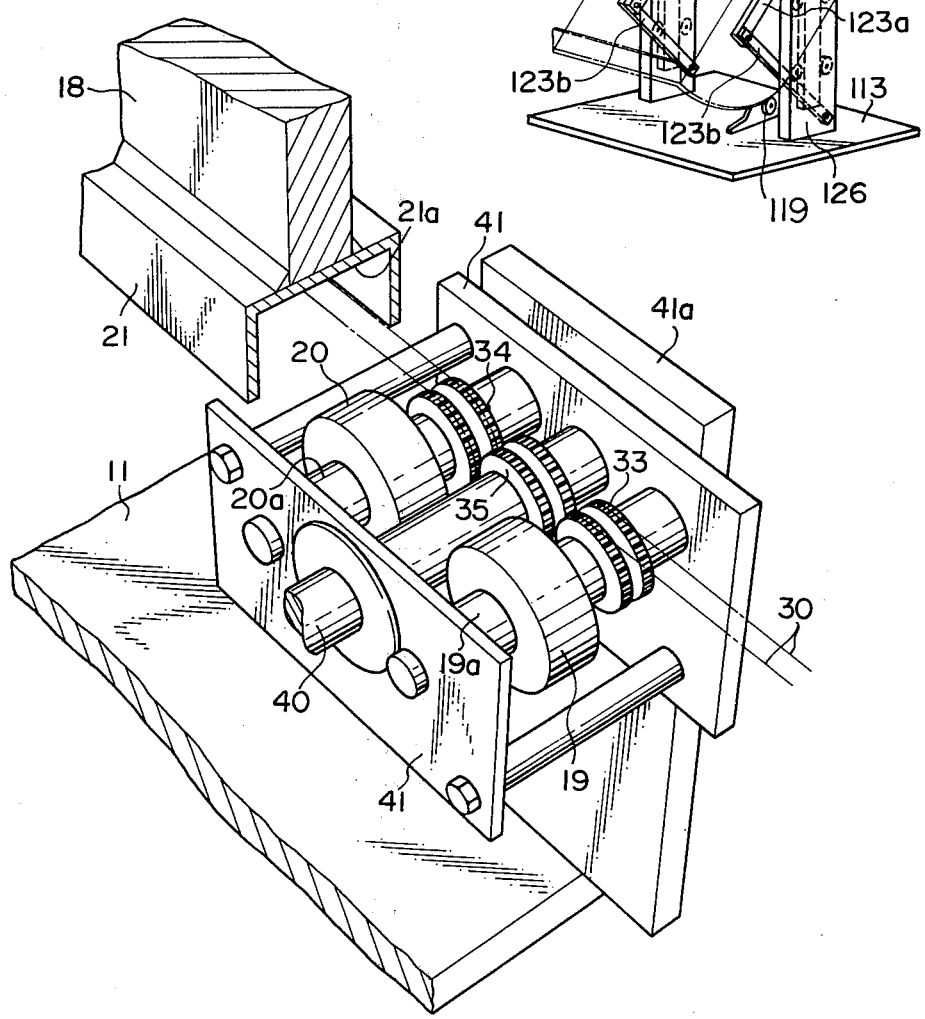

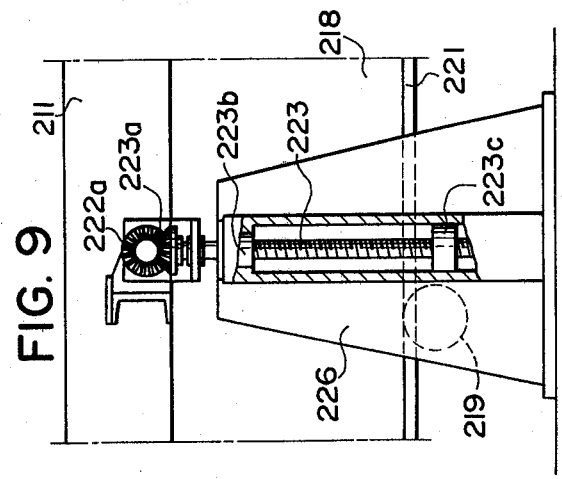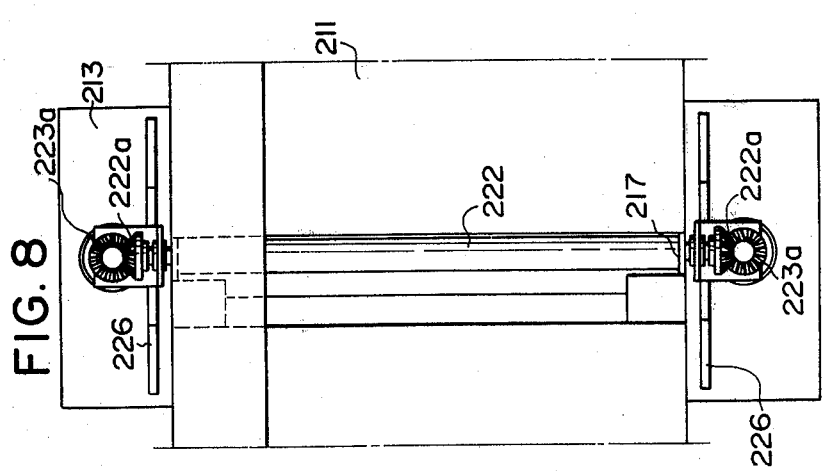

X-RAY APPARATUS

BACKGROUND OF THE INVENTION

(a) Field of the Invention

The present invention concerns an X-ray apparatus, and more particularly it relates to an X-ray apparatus having an improved means of changing the position of the roentgenographic pedestal equipped with a table for receiving a patient thereon.

(b) Description of the Prior Art

A conventional X-ray apparatus is arranged so that a roentgenographic pedestal is supported on a base frame so as to be pivoted, and that an X-ray tube and an X-ray television and photographic unit are arranged on both sides of the patient's table which is provided on top of the roentgenographic pedestal so as to sandwich the table therebetween. The roentgenographic pedestal is arranged so that the pedestal carrying a patient on the table thereof can be held either in a vertical position, or in an inclined position. In order that the roentgenographic pedestal may assume these positions, a huge ring is provided on one lateral side of the pedestal so as to be supported on the base frame. By driving this ring, the roentgenographic pedestal can be rotated through an angle of 360°.

However, such a conventional X-ray apparatus has the drawback and inconvenience that, owing to its arrangement, it cannot be avoided that the distance between the surface of the patient's table and the floor on which the apparatus is installed tends to be great, resulting in a substantial inconvenience for the patient in climbing onto and descending from the patient's table. Besides, due to the fact that one side of the roentgenographic pedestal is occupied by the huge ring, the access to the patient by the operator is rather difficult. As a means of solving such problems, there has been proposed an X-ray apparatus arrangement having a pair of fulcrums for supporting the movement of the patient's table to function, for example, so that the rotation of the roentgenographic pedestal from the vertical position to the horizontal position of the table is performed about one of the two fulcrums and that the rotation of the pedestal from the horizontal position to an inclined position of the table is carried out about the other one of these two fulcrums. According to this previously proposed arrangement, there arises a considerable amount of impact during the switching-over operation from one fulcrum to another. Thus, such an impact would more than a small undesirable psychological effect on the patient.

SUMMARY OF THE INVENTION

It is, therefore, a principal object of the present invention to provide an X-ray apparatus in which the distance between the surface of the patient's table and the floor on which the apparatus is installed is sufficiently small in the horizontal position of the patient's table of the roentgenographical pedestal, and the rotation of the pedestal from the horizontal position to a tilted position and further to the vertical position of the table can be carried out smoothly.

Another object of the present invention is to provide an X-ray apparatus of the type described above, which is such that the operator is able to easily gain access to the patient carried on the patient's table.

Still another object of the present invention is to provide an X-ray apparatus of the type described above, which is compact in size and light in weight.

These as well as other objects and features of the present invention will become apparent by reading the following detailed description of the preferred embodiments of the present invention when taken in conjunction with the accompanying drawings.

BRIEF DESCRIPTION OF THE DRAWINGS

FIGS. 1 through 4 are somewhat diagrammatic representation of an example of the X-ray apparatus of the present invention, in which:

FIG. 1 is a perspective view showing the external appearance of the X-ray apparatus of the present invention as viewed from the front side, looking somewhat down at it;

FIG. 2 is a somewhat diagrammatic rear view of the apparatus shown in FIG. 1 but excluding the patient's table thereof, and with parts broken away;

FIG. 3 is a somewhat diagrammatic plan view of the table in FIG. 2; and

FIG. 4 is a somewhat diagrammatic perspective view showing the details of the supporting and driving portions of the roentgenographic pedestal.

FIGS. 5 through 7 are somewhat diagrammatic representations of another example of the position-changing means employed in the apparatus of the present invention, in which:

FIG. 5 is a somewhat diagrammatic perspective view showing the details of the position-changing means of the roentgenographic pedestal;

FIG. 6 is a somewhat diagrammatic plan view of the apparatus excluding the patient's table and showing only a part of the apparatus; and FIG. 7 is a rear view of same.

FIGS. 8 and 9 are somewhat diagrammatic representations of still another example of the position-changing means employed in the apparatus of the present invention, in which:

FIG. 8 is a somewhat diagrammatic plan view of the apparatus excluding the patient's table and showing only a part of the apparatus; and FIG. 9 is a rear view of the same.

DETAILED DESCRIPTION OF THE PREFERRED EMBODIMENTS

Figure 2:
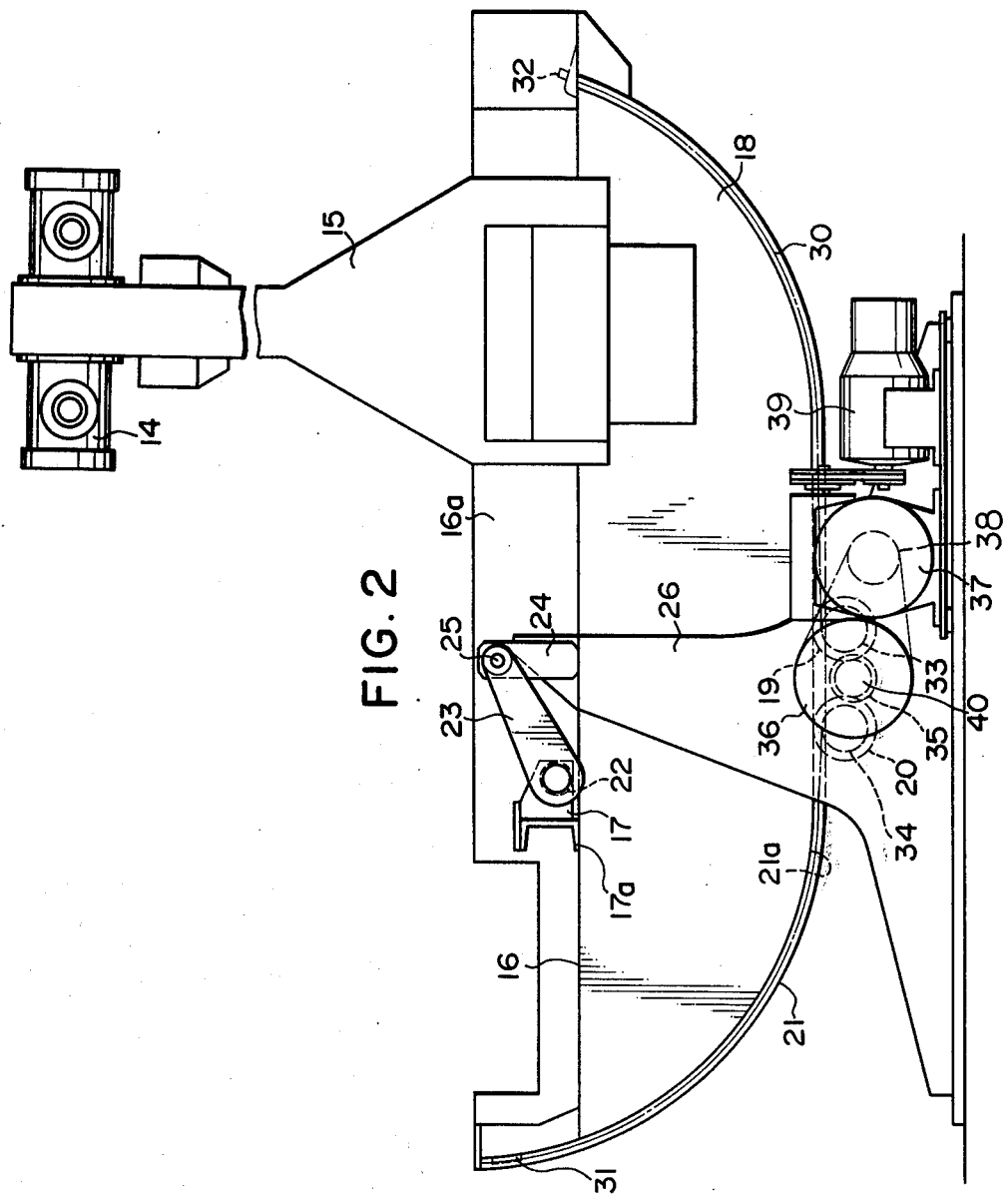

FIG. 1 shows the general arrangement of the X-ray apparatus according to the present invention. A roentgenographic pedestal 11 has a patient's table 12 secured on top thereof, and this pedestal 11 is supported on a base frame 13 in such a way as to allow its swinging movements, i.e. in such a way that the pedestal 11 can be tilted toward the right side, as viewed in the drawing, from its horizontal position which is shown in the drawing, and thereafter swung to assume a vertical position, and therefrom to be tilted toward the right side as viewed in the drawing and then to an oppositely inclined position again. The patient's table 12 is provided so as to move on the roentgenographical pedestal in the longitudinal direction thereof and also in the transverse direction thereof, like the known table of this kind. A column 15 is fixed on a lateral side of the pedestal 11. An X-ray tube 14 is supported on an arm extending from this column 15. Although not shown, an X-ray television and photographic unit is fixed within the roentgenographic pedestal in such a way as to correspond in position to the X-ray tube and with the patient's table 12 positioned between this X-ray television and photographic unit and the X-ray tube.

Figure 3:
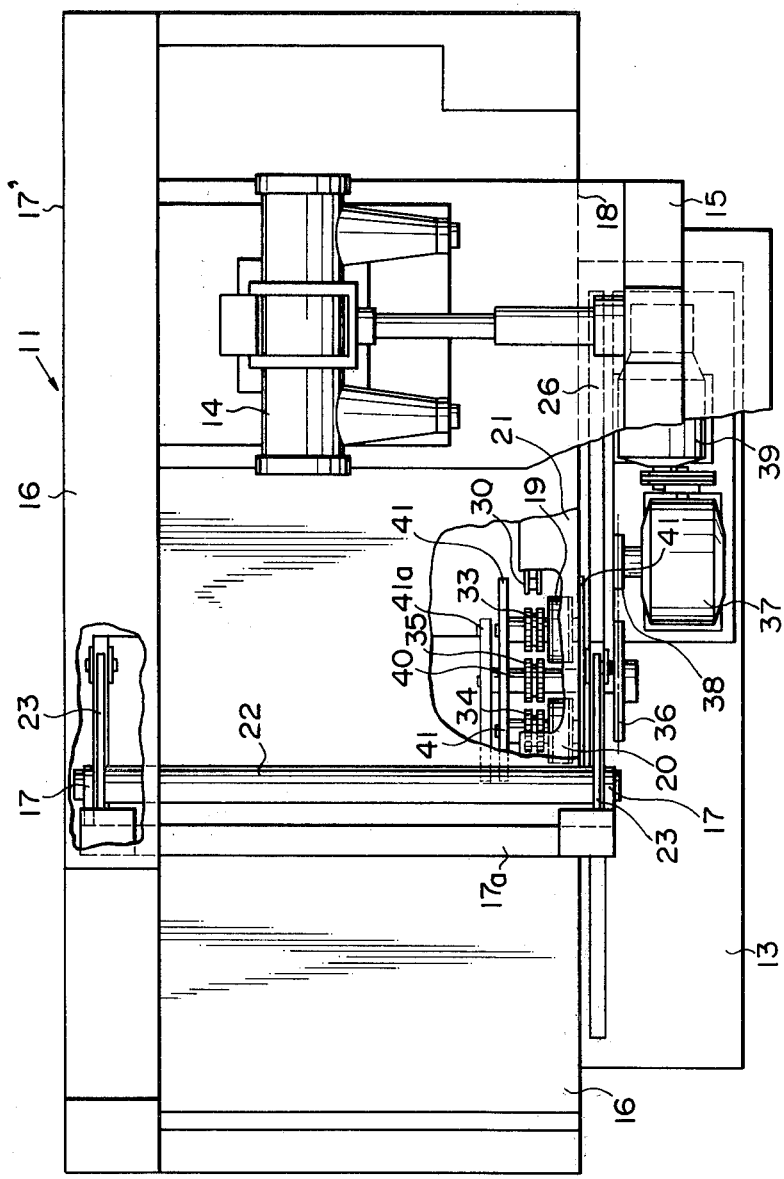

The roentgenographic pedestal 11 is fabricated with angular members and plate members. FIG. 2 is a view taken at the opposite side of the apparatus shown in FIG. 1. As shown in FIGS. 2 and 3, this pedestal 11 is constructed of an upper member 16 and two lateral members 17' and 18 which extend downwardly from the opposing side edges of said upper member. The patient's table is provided, together with its moving means, within the space defined by a wall member 16a which is provided on top of the upper member. This patient's table per se and the moving means therefor are known to those skilled in the art, and therefore, their details are omitted. The X-ray television and photographic unit which is of the well-known type but not illustrated here are arranged on the upper and the lower surfaces of the upper member 16 and is located within the space defined by the lateral members 17' and 18, and in a position corresponding to that of the X-ray tube.

The lateral member 18 in the roentgenographic pedestal 11 concurrently serves as a supporting member for the pedestal. A guide rail 21 is fixed along the end surface of this supporting member 18. As shown in FIG. 4, this guide rail 21 has a channel-shaped cross section. Rollers 19 and 20 support the weight of the roentgenographic pedestal while being in contact with a wall 21a which is parallel with the end surface of said supporting member 18. These rollers 19 and 20 are rotatably supported between two opposing holding plates 41 and 41. As will be described in detail later, these holding plates 41 and 41 are secured to the base frame so as to be rotatable about a shaft 40. As a result, the rollers 19 and 20 are able to tilt about this shaft 40 in a direction transverse to the axes of rollers 19 and 20.

On the upper member 16 is arranged a shaft 22 extending transverse to the direction of the positional changing movements of the roentgenographic pedestal 11. More specifically, the shaft 22 is arranged to extend in the transverse direction of the roentgenographic pedestal. The opposite ends of this shaft 22 are rotatably supported by bearings provided on the plates 17 and 17, respectively. These plates 17 and 17 are fixed to a member 17a which, in turn, is fixed to the upper portion of the upper member 16. Each of the arms 23 and 23 has one of its ends secured to said shaft 22. The free ends of these arms 23 are supported by pins 25 on one end of arms 24 which are fixed to supporting legs 26 which constitute the base frame 13. The rotary shaft for the bearings of the supporting legs and the shafts of the pins 25 are arranged so as to be parallel with the shaft 22. Because of these arrangements, the roentgenographic pedestal is capable of making a swinging movement about the shaft 22 on the rollers 19 and 20. At the same time, the arms 23 serve to hold the pedestal 11 onto the base frame 13, and also the arms 24 act to restrict the direction of movement of this pedestal 11.

Since one of the lateral members 17' and 18 itself is comprised of curved portions extending from the upper member 16 and a flat portion which is parallel with the surface of the patient's table and joins at its opposite ends to the ends of said curved portions, it will be understood that the surface 21a of contact between the guide rail 21 of the pedestal 11 and the rollers 19 and 20 is comprised also of curved portions and a flat portion which correspond to the above-said curved portions and flat portion, respectively. Therefore, when the rollers 19 and 20 are in contact with the flat portion contained in the surface of contact of the guide rail 21 of the pedestal 11, as shown, the surface of the table 12 provided on the roentgenographic pedestal 11 is horizontal. When the pedestal 11 is urged either toward the left side or toward the right side in FIG. 2 starting from said horizontal position of the table 12, the pedestal 11 will move progressively while in contact with the rollers 19 and 20, so that eventually these rollers 19 and 20 will contact either one of the curved portions of the surface of contact of the guide rail 21 of the pedestal 11. As a result, this pedestal will be caused to tilt into a posture which is restricted and produced by the one of the curved portions which has been contacted. By a further movement, the pedestal 11 and accordingly the table 12 will be brought to a vertical position. During these changes in the position of the pedestal 11, the two rollers 19 and 20 jointly are inclined about the shaft 40. The arms 23, at the same time as the inclining of the assembly of these rollers, act so as to restrict the direction of movement of the pedestal 11. Thus, the contact between the guide rail 21 and the rollers 19 and 20 is maintained.

The movement of the roentgenographic pedestal 11 is carried out by driving a chain 30 which is arranged along the surface of contact 21a of the guide rail 21. Although illustrated in a simplified manner, the chain 30 is comprised of a roller chain. The opposite ends of this chain 30 are fixed by stops 31 and 32 to the pedestal 11 at positions close to the upper member 16. As best shown in FIG. 4, this chain engages sprockets 33 and 34 and also a driving sprocket 35 all of which are arranged below the pedestal 11. The sprockets 33 and 34 are provided on the shafts 19a and 20a carrying the rollers 19 and 20, respectively. The driving sprocket 35 is fixed to a shaft 40. These shafts 19a, 20a and 40 are supported by bearings on the holding plates 41 and 41. This shaft 40, furthermore, is supported at one end, by a bearing, on a supporting plate 41a which constitutes a part of the base frame 13, and at the other end is supported, by a bearing, on a supporting leg 26 which also constitutes a part of the base frame 13. Because of this arrangement, the holding plates 41 are able to rotate, jointly with the shafts 19a and 20a, about the shaft 40, and the assembly of the rollers 19 and 20 can be swung about the shaft 40 or rotated about this shaft 40, so that these rollers 19 and 20 thus can be tilted.

To the above-said other end of the shaft 40 is fixed said sprocket 36. This sprocket 36 is connected, by a chain, with a sprocket 38 of the output shaft of a speed reduction gear 37 which, in turn, is mounted on the base frame 13. The input shaft of this speed reduction gear 37 is connected, by a belt and a pulley, with a motor 39. This motor 39 is comprised of a well-known motor equipped with braking means.

This motor 39 is arranged so that, upon being started, its brake is released so that the shaft 40 begins to rotate via the speed reducing gear. The rotation of the sprocket 35 results in the driving of the chain 30. Thereby the roentgenographic pedestal 11 is swung about the shaft 22. Along with this swinging movement of the pedestal 11, the rollers 19 and 20 are tilted about the shaft 40. At the same time, the arms 23 are rotated about their pins so that the roentgenographic pedestal 11 is caused to assume either the horizontal position, or an inclined posture or a vertical position, as desired. The motor 39 is brought to a halt at the moment the pedestal 11 is brought into the required position. At that time, the brake acts to hold the pedestal 11 in the required position. When the motor 39 is rotated in the reverse direction, the pedestal 11 is swung in the reverse direction about the shaft 22. Along therewith, the arms 23 are rotated about the pins 25. Thus, the rollers 19 and 20 are again brought into contact with the flat portion contained in the surface of contact of the guide rail 21, so that the pedestal 11 is brought to the horizontal position. By further rotating the motor 39, the pedestal 11 is caused to incline, with its table surface now facing the opposite side relative to the above-stated instance.

In the X-ray apparatus according to the present invention, it will be understood that, in accordance with the changes in the position of contact between the surface of contact of the guide rail 21 and the rollers 19 and 20, the roentgenographic pedestal 11 will change its position. For this reason, it is possible to cause the roentgenographic pedestal 11 to assume various different or modified positions or movements including those described above by selecting the contour of the supporting member, i.e. the lateral member 18.

When the roentgenographic pedestal 11 is in its horizontal position, the distance between the surface of the table 12 and the floor on which the apparatus is installed is determined principally by the distance between the surface of the table 12 and the surface of contact of the guide rail 21. The minimum distance thereof may be said to depend entirely on the height of the X-ray television and photographic unit which is housed within the roentgenographic pedestal 11. For this reason, the distance between the surface of the table 12 of the pedestal 11 and the floor in the horizontal position of the pedestal 11 can be greatly reduced. Thereby, the mounting onto the table 12 and the stepping down from the table by the patient becomes extremely easy. In addition, the lateral side of the roentgenographic pedestal 11 is occupied only by the column assigned to support the X-ray tube. Moreover, this column need support only the X-ray tube. As such, the operator is able to gain easy access to the patient at either desired side of the pedestal. This fact plus the minimized distance discussed above enable the X-ray apparatus as a whole to be constructed in a very compact size.

FIGS. 5 through 7 show another example of the position-changing means of the roentgenographic pedestal, according to the present invention. A roentgenographic pedestal 111 has the same construction as that of the preceding example with the following exception. In this instant example, the roentgenographic pedestal 111 is so arranged that its guide rail 121 which is formed on a lateral member 118 is in contact with a roller 119 which, in turn, is rotatably supported on a base frame 113, and also that said guide rail 121 and accordingly the pedestal 111 are thus supported on top of this roller 119. In this example however, the roller 119 is mounted on the base frame 113 in such a way that it is not allowed to be tilted.

A shaft 122 is arranged in the transverse direction of the pedestal 111. This pedestal 111 is swingably supported on bearings provided on supporting plates which are fixed to an upper member of the pedestal 111. This shaft 122 further is supported at its opposite ends at the end portions of rods 124 in bearings. These rods 124 are held on supporting legs 126 which extend from the base frame 113 in such a way as to be movable only longitudinally of these rods. Arms 123a are attached, at one end thereof, to the shaft 122 via bearings. Arms 123b are attached at one end thereof to supporting legs 126 and 126 via bearings, respectively. The other ends of these paired arms are coupled to each other by pins, respectively. The axes of rotation of the shafts of these bearings and the shafts of the pins are arranged in parallel with the shaft 122. As stated previously, the shaft of the roller 119 is supported on the base frame directly via a bearing. Said shaft of the roller 119 is associated with a motor equipped with a braking means, via an appropriate train of gears not shown, in such a manner that as the motor rotates, the roller 119 conducts frictional drive of the roentgenographic pedestal 111. Let us now assume that, in the horizontal position of the pedestal 111 as shown in FIGS. 6 and 7, the motor is started. Whereupon, the pedestal 111 will be caused to swing about the shaft 122. As a result, the shaft 122 will move upwardly. At the same time therewith, the arms 123a, and 123b are caused to rotate. This rotation of the arms will cause the pedestal 111 to move while maintaining the contact between the guide rail 121 and the roller 119. As the motor continues its rotation, the pedestal 111 will become inclined, and from this position, the pedestal 111 will progressively change its position onto a vertical posture. By rotating the motor in the reverse direction, the pedestal 111 will be swung in the reverse direction. After passing the horizontal position, the pedestal 111 will become inclined in the reverse direction of the preceding inclined posture. It will be apparent to those skilled in the art that in the position-changing device employed in this instant example, the swinging movement of the roentgenographic pedestal 111 can be carried out by the use of a chain in a manner similar to that described in connection with the preceding example.

FIGS. 8 and 9 show still another example of the position-changing device employed in the apparatus of the present invention. In this instant example, a shaft 222 is fixed, by supporting plates 217 to a roentgenographic pedestal 211. A roller 219 is in contact with a guide rail 221 of the pedestal 211. As this roller 219 rotates, the roentgenographic pedestal 211 is swung about the shaft 222. Such operation is similar to that described in connection with the example of FIGS. 5 through 7, with the following exceptions. In the instant example, bevel gears 222a are mounted on the opposite ends of the shaft 222. These bevel gears 222a engage the bevel gears 223a on threaded rods 223 of a well-known type, respectively. The threaded rod herein employed is a combination of a threaded rod and a correspondingly threaded nut carrying balls in the thread of the nut so that the balls are recirculated in the coil-shape space defined between the threads of the rod and the nut. The nuts 223b of these threaded rods 223 are fixed to casings which, in turn, are fixed to supporting legs 226, respectively. As the roller 219 rotates, the roentgenographic pedestal 211 is swung about the shaft 222. Whereupon, the shaft 222 is caused to ascend upwardly while rotating. The rotation of this shaft 222 will cause the threaded rods 223 to rotate through the bevel gears, respectively. Thereby, the threaded rods 223 will move, jointly with bushings 223c, in accordance with the ascension of the shaft 222, so that the direction of movement of the roentgenographic pedestal 211 will be restricted.

I claim:
1. An X-ray apparatus comprising;
a base frame;
a roentgenographic pedestal having a patient's table thereon;

an X-ray source and an X-ray television and/or photographic unit in spaced opposed relationship with said patient's table therebetween; and means for changing the position of said pedestal, said position changing means comprising: a supporting member extending away from the bottom side of said patent's table; a guide rail provided on the periphery of the end of said supporting member, said guide rail having a contact surface with a contour having at least one curved portion protruding in a direction away from the surface of the patient's table and a flat portion joining one end of said curved portion; at least one roller in contact with said guide rail for supporting the weight of said pedestal said roller being mounted for tilting movement transverse to the axis of rotation thereof; and supporting means for causing the pedestal to move only along the guide rail while in contact with said roller, said supporting means having a shaft extending in a direction transverse to the direction of movement of said pedestal and being rotatably supported on the pedestal, and at least one arm extending from said shaft and pivotably supported on said base frame, whereby the position of the pedestal is changed in accordance with the contour of the guide rail.

2. An X-ray apparatus according to claim 1 in which said roentgenographic pedestal has a chain extending along the contact surface of said guide rail and being fixed at the opposite ends thereof to the pedestal at positions close to the patient's table, and a sprocket rotatably mounted on the base frame and meshed with said chain, whereby the pedestal is moved by the rotation of said sprocket.

3. An X-ray apparatus comprising;
a base frame;
a roentgenographic pedestal having a patient's table thereon;
an X-ray source and an X-ray television and/or photographic unit in spaced opposed relationship with said patient's table therebetween; and
means for changing the position of said pedestal, said position changing means comprising: a supporting member extending away from the bottom side of said patient's table; a guide rail provided on the periphery of the end of said supporting member, said guide rail having a contact surface with a contour having at least one curved portion protruding in a direction away from the surface of the patient's table and a flat portion joining one end of said curved portion; at least one roller in contact with said guide rail for supporting the weight of said pedestal; and supporting means for causing the pedestal to move only along the guide rail while in contact with said roller, said supporting means having a shaft rotatably supported on said pedestal and extending transversely of the pedestal, a rod movably mounted on said base frame for movement only vertically of said base frame, a first arm pivotably mounted on said shaft, and a second arm pivotably mounted on the base frame and pivotably coupled to said first arm, whereby the position of said pedestal is changed in accordance with the contour of the guide rail.

4. An X-ray apparatus according to claim 3 further comprising a motor and means connecting said motor and said roller for driving said roller for moving the pedestal in accordance with the rotation of said motor.

5. An X-ray apparatus comprising;
a base frame;
a roentgenographic pedestal having a patient's table thereon;
an X-ray source and an X-ray television and/or photographic unit in spaced opposed relationship with said patient's table therebetween; and
means for changing the position of said pedestal, said position changing means comprising: a supporting member extending away from the bottom side of said patient's table; a guide rail provided on the periphery of the end of said supporting member, said guide rail having a contact surface with a contour having at least one curved portion protruding in a direction away from the surface of the patient's table and a flat portion joining one end of said curved portion; at least one roller in contact with said guide rail for supporting the weight of said pedestal; and supporting means for causing the pedestal to move only along the guide rail while in contact with said roller, said supporting means having a shaft extending transversely of said pedestal and rotatably supported thereon, a vertically movable threaded rod on said base frame, and bevel gears connecting said threaded rod and said shaft, whereby the position of said pedestal is changed in accordance with the contour of the guide rail.

* * * * *